United States Patent
Owades

(10) Patent No.: US 6,284,244 B1
(45) Date of Patent: Sep. 4, 2001

(54) MEDIATING THE EFFECTS OF ALCOHOL CONSUMPTION BY ORALLY ADMINISTERING ACTIVE DRY YEAST

(76) Inventor: Joseph L. Owades, 3097 Wood Valley Rd., Sonoma, CA (US) 95476

( * ) Notice: Subject to any disclaimer, the term of this patent is extended or adjusted under 35 U.S.C. 154(b) by 0 days.

(21) Appl. No.: 09/513,022

(22) Filed: Feb. 25, 2000

(51) Int. Cl.⁷ ............... A01N 63/00; C12N 1/16
(52) U.S. Cl. .................... 424/93.51; 435/255.1; 435/255.2
(58) Field of Search ............ 424/94.4, 93.51; 435/255.1, 255.2

(56) References Cited

U.S. PATENT DOCUMENTS

| | | | |
|---|---|---|---|
| 3,954,979 | * 5/1976 | Bowman | 424/195.1 |
| 4,006,219 | * 2/1977 | Upham et al. | 424/94.1 |
| 4,450,153 | 5/1984 | Hopkins | 424/94.4 |
| 6,007,809 | * 12/1999 | Chaykin | 424/93.51 |

* cited by examiner

*Primary Examiner*—David M. Naff
*Assistant Examiner*—Mike Meller
(74) *Attorney, Agent, or Firm*—Hayes, Soloway, Hennessey, Grossman & Hage, PC

(57) ABSTRACT

Mediating the effects of alcohol consumption by orally administering an active dry yeast containing alcohol dehydrogenase to a person prior to or simultaneously with consumption of an alcohol-containing beverage to oxidize a portion of the alcohol while it is still in the stomach of the person is described.

5 Claims, 4 Drawing Sheets

MEDIATING THE EFFECTS OF ALCOHOL CONSUMPTION BY ORALLY ADMINISTERING ACTIVE DRY YEAST

FIELD OF THE INVENTION

The present invention relates to a process for lowering of blood alcohol (i.e. ethyl alcohol) levels in humans after they imbibe alcoholic beverages such as beer, wine or distilled spirits.

BACKGROUND OF THE INVENTION

Consumption of alcoholic beverages in moderate amounts is an accepted societal practice. Additionally, consumption of alcoholic beverages in moderate amounts is considered to provide some health benefits in terms of reduced stress and incidence of heart attack. Consumption of alcoholic beverages in moderate amounts also is considered by many people to enhance the flavor and enjoyment of food. However, even moderate social drinkers can be affected by alcohol. Ethyl alcohol ($CH_3CH_2OH$) is a major purpose for the consumption of alcoholic beverages. When such beverages are consumed, the alcohol enters the stomach and is soon transported to the small intestine. From here the alcohol enters the blood stream via the portal vein and goes to the liver. Here, a portion of the alcohol is oxidized to acetaldehyde by the enzyme alcohol dehydrogenase. The unoxidized alcohol goes to every part of the body through the general circulation. This alcohol, which has free access to every cell in the body, exerts an influence on the central nervous system and the brain. These effects are well known. Operation of a motor vehicle is considered illegal if the level of alcohol in the blood (blood alcohol level) is above 0.1% (in some states) or 0.08% (in other states). Because alcohol diffuses into every cell in the body freely, the blood alcohol level may be measured in the breath as well as in the blood. The acetaldehyde produced is further oxidized almost instantaneously to acetate which enters the pathways of general metabolism. Acetaldehyde and acetate have no effect on the nervous system or the brain. Continued circulation through the liver eventually removes all the alcohol.

The enzyme alcohol dehydrogenase requires a coenzyme called nicotinamide adenine dinucleotide (NAD) in order to catalyze the conversion of ethanol to acetaldehyde. The first step in the metabolism of ethanol can be shown by the following equation:

(1)

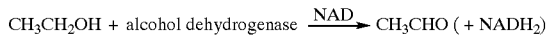

U.S. Pat. No. 4,450,153 to Hopkins proposes a process for reducing the effects of alcohol consumption by reducing the alcohol content in human blood by the administration of alcohol oxidase. According to Hopkins, alcohol oxidase may be administered by direct injection into the human body, or by direct contact with the blood by means of dialysis. Hopkins also suggests that alcohol oxidase may be administered orally; however, Hopkins needs his alcohol oxidase to be enteric coated to protect it from being destroyed in the stomach. He does not reduce alcohol levels in the stomach. He actively avoids this.

It is therefore an object of the present invention to provide a process for the reduction of human blood alcohol level by attacking alcohol only in the stomach.

BRIEF DESCRIPTION OF THE INVENTION

In accordance with the present invention, blood alcohol level is lowered by the oral administration of an extraneous source of the enzyme alcohol dehydrogenase before or concomitantly with the drinking of the alcoholic beverage. The alcohol dehydrogenase may be consumed as the purified enzyme, or more conveniently, by the ingestion of a natural source of the enzyme, such as active dry bakers, brewers, vintners or distillers yeast. As used herein, active bakers, vintners and distillers yeast comprise *Saccharomyces cerevisiae*, and active brewers yeast comprises *Saccharomyces uvarum*. These yeasts all contain alcohol dehydrogenase and nicotinamide adenine dinucleotide (NAD). These yeasts may be delivered in powdered, paste or liquid form, i.e. suspended in a liquid, but most conveniently are packaged in dose or portion controlled dried form as a tablet or caplet, or in capsule form.

It has been found that ingesting active dry bakers yeast (the yeast most readily available commercially) or brewers, vintners or distillers yeast, just before, or during, the drinking of an alcoholic beverage, oxidizes a portion of the alcohol while still in the stomach, which results in a lower peak blood alcohol level, and also a lesser area under the curve of a plot of blood alcohol level vs. time. The action of the alcohol dehydrogenase on the alcohol is only in the stomach, so the alcohol dehydrogenase source must be ingested while the alcoholic beverage is still in the stomach. It will have no effect once the alcohol has left the stomach and entered the bloodstream, because the enzyme is destroyed by the acidity and proteolytic action in the stomach.

BRIEF DESCRIPTION OF THE DRAWINGS

Other features and advantages of the present invention will be seen from the following detailed description, taken in conjunction with the accompanying drawings, wherein.

DETAILED DESCRIPTION OF PREFERRED EMBODIMENTS

Figure 1:
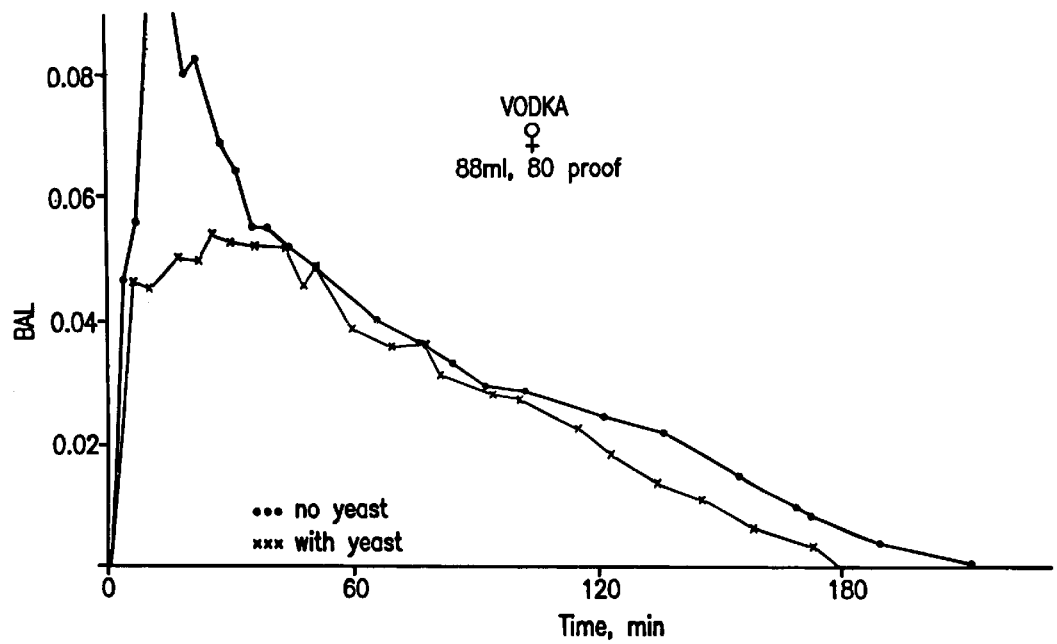
FIGS. 1–8 are plots showing reduction of blood alcohol levels over time with several alcoholic beverages, with and without the ingestion of alcohol dehydrogenase from active dry yeast.

As noted supra, when an alcoholic beverage is consumed, the alcohol enters the stomach and is soon transported to the small intestine. The speed of egress from the stomach is delayed by the presence of food or fats in the stomach, and by the dilution and buffering capacity of the alcoholic liquid. The speed of the egress from the stomach is quickened by high concentration of the alcoholic drink and by carbon dioxide in the drink. In the small intestine, the alcohol is absorbed into the blood stream via the portal vein and goes to the liver. In accordance with the present invention, a portion of the alcohol while still in the stomach is oxidized to acetaldehyde by the ingestion of an extraneous source of the enzyme alcohol dehydrogenase.

Ingestion of the enzyme alcohol dehydrogenase in accordance with the present invention may be before or concomitantly with the consumption of the alcoholic beverage. Continued drinking requires the periodic ingestion of additional alcohol dehydrogenase during the drinking period. The amount of alcohol dehydrogenase which should be ingested to reduce the blood alcohol level to an acceptable level depends on several factors:

the weight of the individual;
the sex of the individual;
the amount of alcohol consumed;
the rate of alcohol consumption;

the general health and age of the individual; and the presence of food in the stomach.

Generally, the alcohol dehydrogenase is ingested in the amount of 0.5 to 10 grams of active dry bakers, brewers, distillers or vintners yeast. The amount needed is determined by the six factors listed above, and the idiosyncratic behavior of different people to alcohol. While the alcohol dehydrogenase may be ingested, for example, as a suspension in a liquid or paste, the most convenient and effective way to administer the alcohol dehydrogenase is by means of dose controlled tablets, capsules or caplets containing active dry bakers, brewers, vintners or distillers yeast. The advantage of ingesting the alcohol dehydrogenase in this manner is that it permits the drinker to self-dose during the imbibition period. Since the ingested alcohol dehydrogenase does not long survive in the acidity of and in the presence of the proteolytic enzymes in the stomach, the ingested alcohol dehydrogenase has no effect beyond the stomach.

A further understanding of the invention will be seen from the following working Examples, in which blood alcohol content was measured using an Alco-Sensor III blood alcohol content breath analyzer, available from Intoximeters, Inc., St. Louis, Mo. The alcohol dehydrogenase was administered as active dry bakers yeast available from Fleischmann's Yeast Division of Burns Philp Food, Inc., Fenton, Mo., Red Star Yeast from Universal Foods, Milwaukee, Wis. and a wine yeast from Lallemand, Montreal, Canada.

EXAMPLE I

Eighty-eight milliliters of 80 proof vodka, diluted with 80 ml. of water are consumed by a young, 160 pound adult woman, within 5 minutes. The alcohol content in the breath, directly proportional to the blood alcohol level, is measured periodically until the level falls below 0.002%.

The experiment is repeated, with the same woman, but this time, 2.5 g. of active dry bakers yeast is ingested followed by 88 ml. of 80 proof vodka diluted with 80 ml of water. The alcohol content in the breath is measured periodically.

The results for both tests are shown in FIG. 1 and show the decrease in blood alcohol level caused by the yeast. The decrease, as measured by the areas under the curves in blood alcohol level - min. was 29%.

EXAMPLE II

The same tests, without and with the ingestion of 2.5 g. of active dry bakers yeast were done. This time the tests were run with a young, 155 pound adult man.

Figure 2:
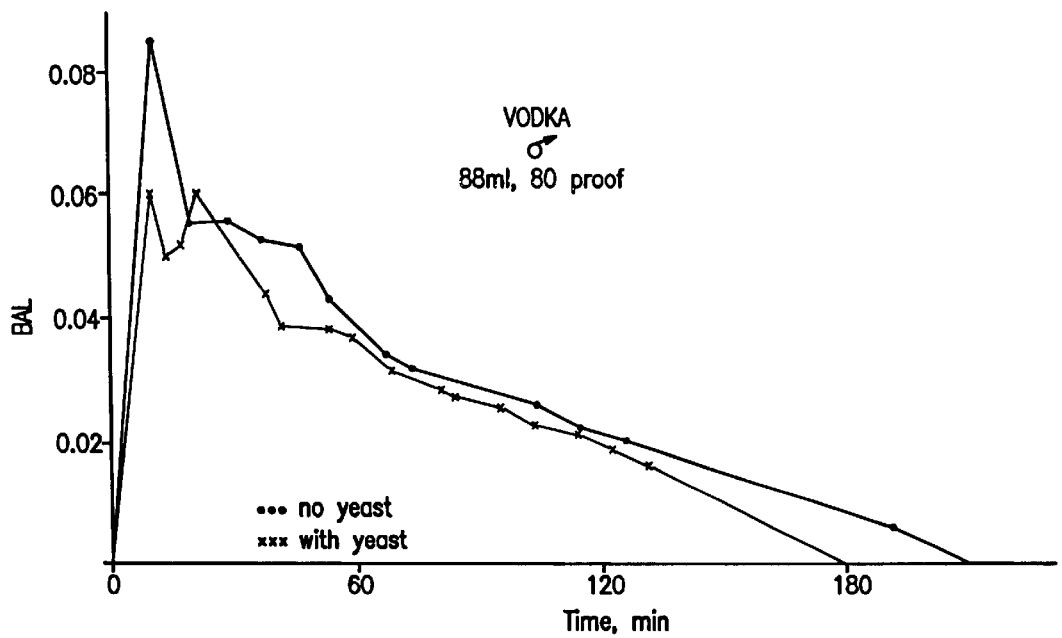

The results for both tests are shown in FIG. 2. The decrease in blood alcohol level when the yeast was taken is clearly shown, and quantitatively demonstrated by the reduction in blood alcohol level-min. of 23% in the areas under the curves.

EXAMPLE III

A mature 170 pound adult man consumed 268 ml. of chardonnay wine, 13% alcohol by volume in 11 minutes. His blood alcohol level was measured periodically.

The test was repeated, by the same man, but this time 2.5 g. of active dry vintners yeast was ingested just before the wine was consumed. The blood alcohol level was measured periodically.

Figure 3:
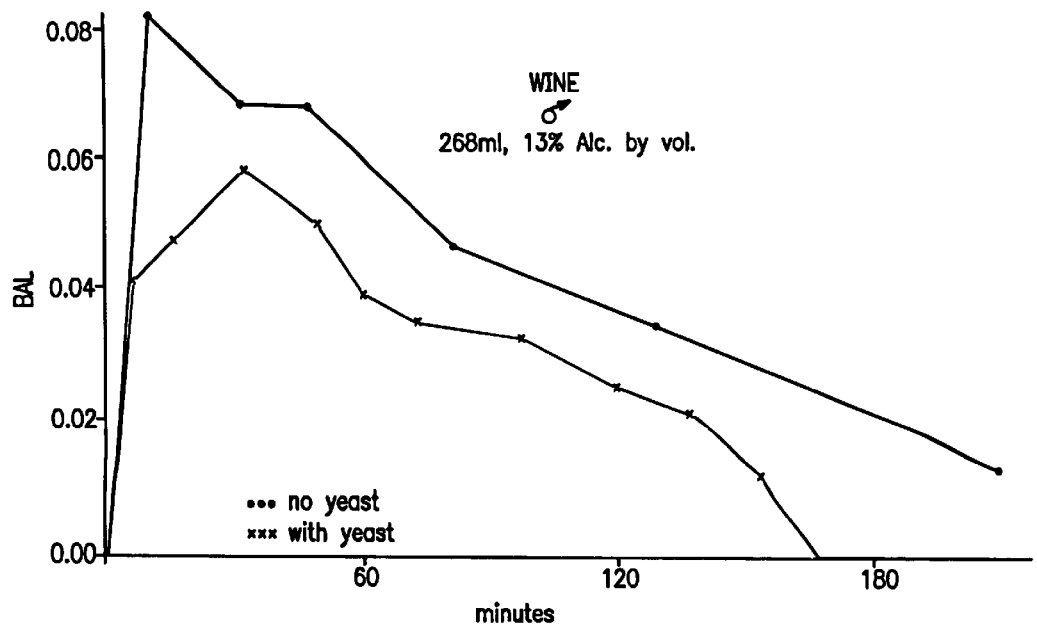

The results are shown in FIG. 3. The ingestion of the yeast lowered the peak level and decreased the area under the curve, in blood alcohol level-min. by 36%.

EXAMPLE IV

A mature, 170 pound woman performed the same tests as in Example III.

Figure 4:
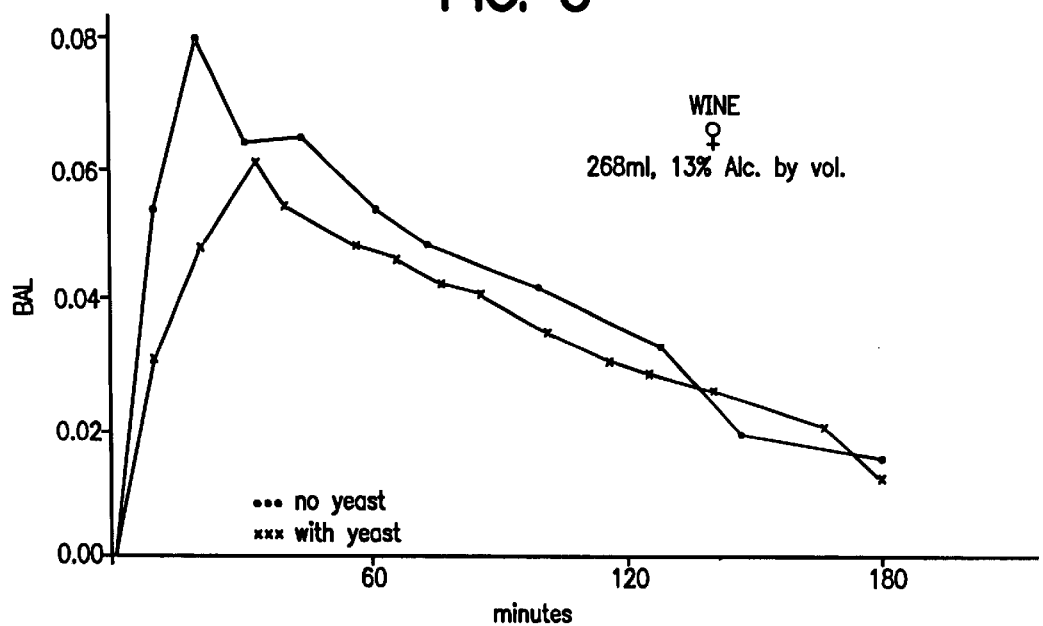

The results are plotted in FIG. 4. The areas under the curve, in blood alcohol level-min., decreased by 21% when the yeast was taken just before the wine was consumed.

EXAMPLE V

Seven hundred and ten ml. (24 oz.) of a standard American beer (5% alcohol by volume) was consumed by a mature, 150 pound adult woman in 13 minutes, and then the blood alcohol level was measured periodically.

The same woman ate 5.0 g. of active dry bakers yeast and then drank the same volume of the same beer. The blood alcohol was measured periodically.

Figure 5:
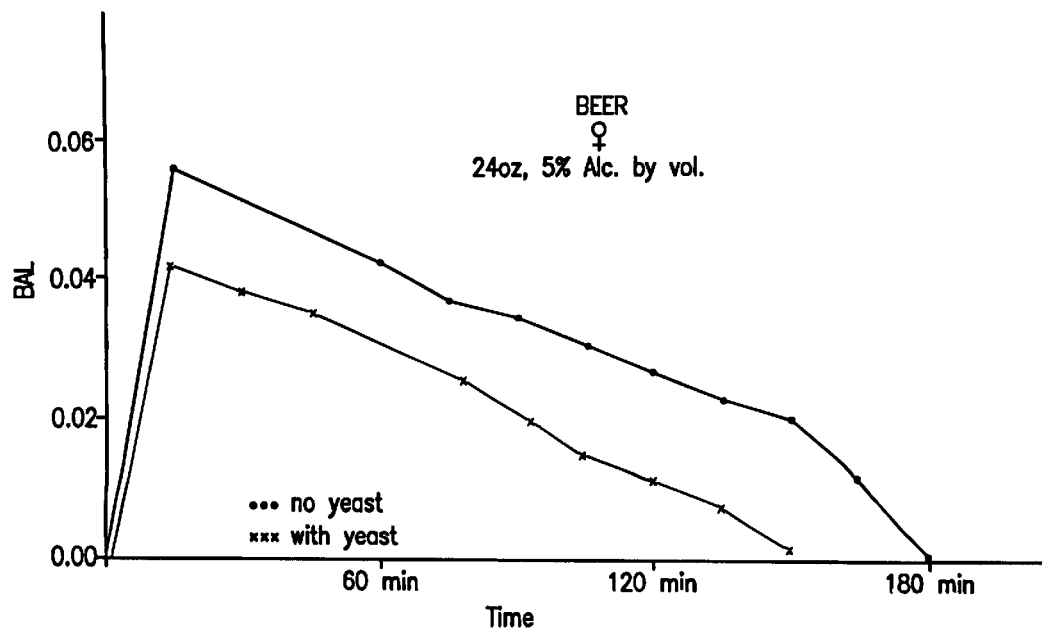

The results are shown in FIG. 5. The yeast reduced the area under the curve, in blood alcohol level-min., by 26%.

EXAMPLE VI

Twenty-four ounces of a standard American beer, the same as in Example V, was consumed by a mature, 140 pound adult man in 8 minutes. His blood alcohol level was measured periodically.

The same amount of the same beer was consumed by the same man, except 2.5 g. of active dry bakers yeast was taken at the start of the beer drinking, which was finished in 14 minutes. Blood alcohol levels were measured periodically.

Figure 6:
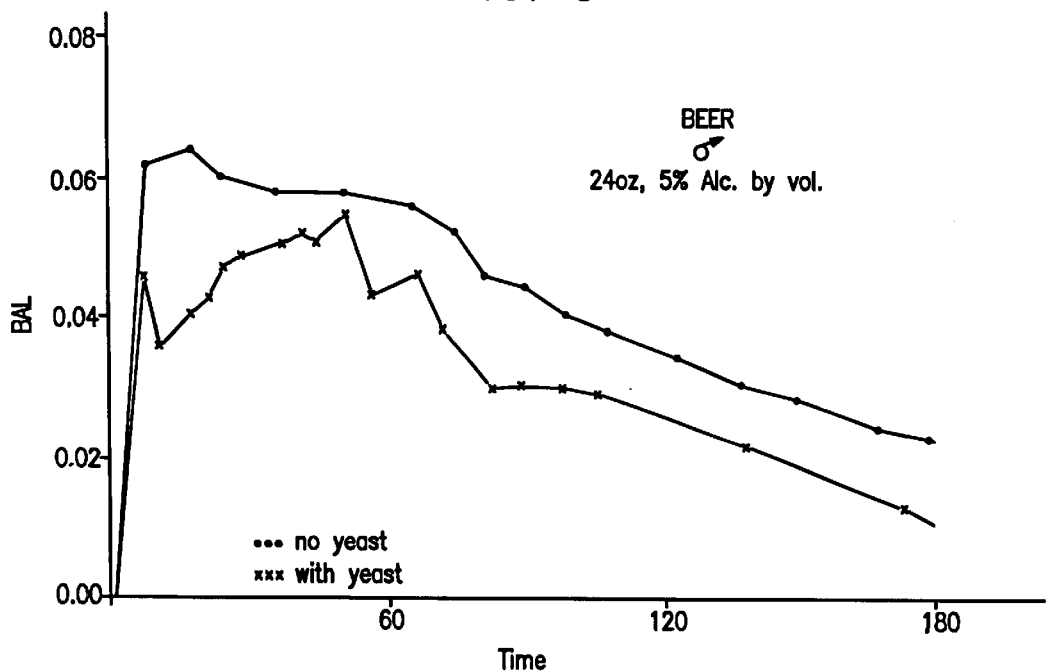

The results of both tests are shown in FIG. 6. The area under the curve, in blood alcohol level-min., was reduced by 30% by the yeast.

EXAMPLE VII

Twenty-four ounces of a light beer, alcohol content 4.2% by volume, was consumed by a mature, 150 pound adult woman, after 3.0 g. of active dry brewers yeast was ingested, all in 15 min. The blood alcohol level was measured periodically.

The same amount of the same beer was consumed by the same woman, but without any yeast.

Figure 7:
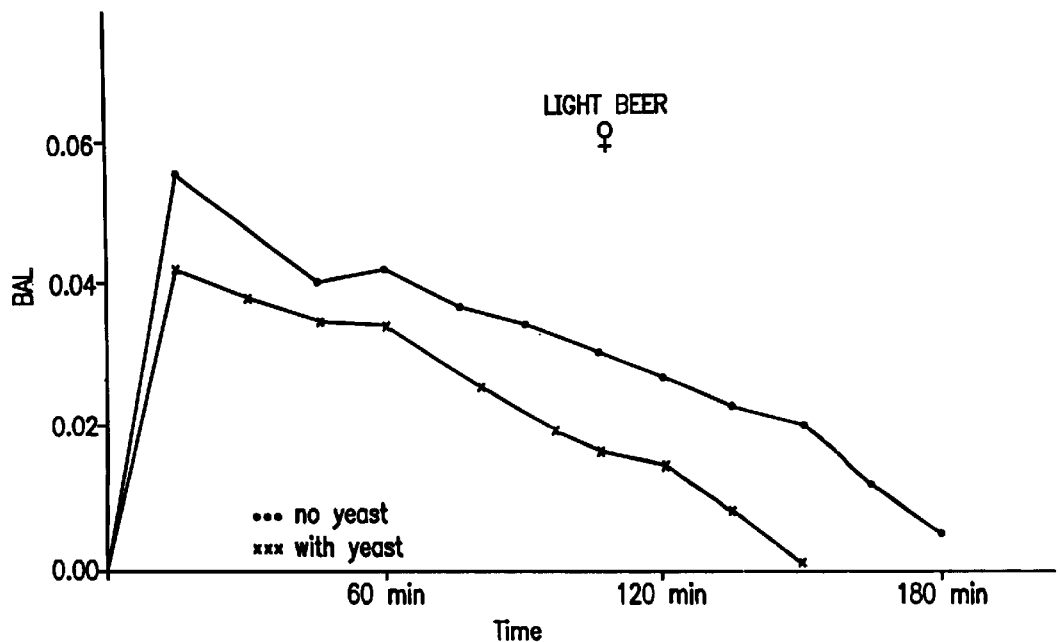

The results of both tests, are shown in FIG. 7. The area under the curve, in blood alcohol level-min. was reduced by 38% by the yeast.

EXAMPLE VIII

A mature, 155 pound adult man consumed 24 oz. of the same beer as in Example VII, right with the ingestion of 1.5 g. of active dry bakers yeast. His blood alcohol level was measured periodically.

The above test was repeated, but without ingestion of any yeast.

Figure 8:
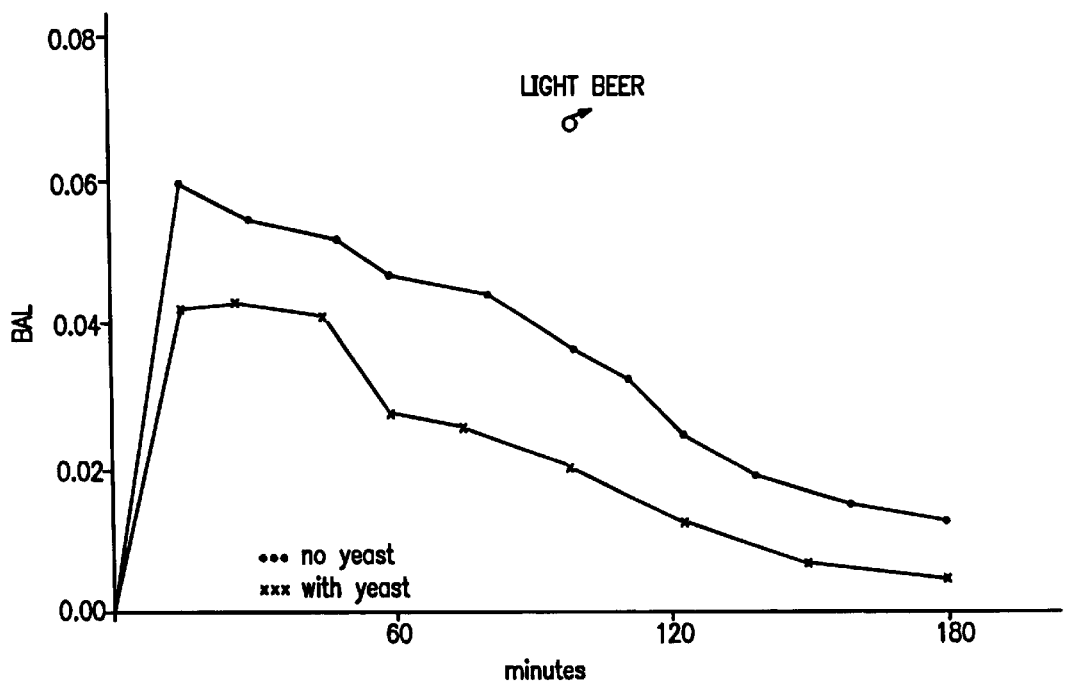

The results are shown in FIG. 8. The area under the curve, in blood alcohol level-min., was reduced by 38% when yeast was taken.

Various changes may be made in the foregoing invention without departing from the spirit and scope thereof.

What is claimed is:

1. A method of mediating the effect of alcohol consumption by a person which consista essentially of orally administering active dry yeast containing alcohol dehydrogenase to said person prior to or simultaneously with consumption of an alcohol-containing beverage, whereby to oxidize a portion of the alcohol while still in the stomach of said person.

2. A method according to claim 1, wherein said active dry yeast is administered in a dose of from 0.5 to 10 grams.

3. A method according to claim 1, wherein said active dry yeast is selected from the group consisting of active yeast, active dry brewers yeast, active dry vintners yeast, and active dry distillers yeast.

4. A method according to claim 1, wherein said active dry yeast is administered in tablet, caplet or capsule form.

5. A method according to claim 1, wherein said active dry yeast is consumed as a powder, paste or liquid.

* * * * *

UNITED STATES PATENT AND TRADEMARK OFFICE
CERTIFICATE OF CORRECTION

PATENT NO. : 6,284,244 B1
DATED : September 4, 2001
INVENTOR(S) : Owades

Page 1 of 1

It is certified that error appears in the above-identified patent and that said Letters Patent is hereby corrected as shown below:

Column 2,
Line 62, "consista" should be -- consists --

Signed and Sealed this

Fourth Day of June, 2002

*Attest:*

*Attesting Officer*

JAMES E. ROGAN
*Director of the United States Patent and Trademark Office*